(12) United States Patent
Toplak Casar (10) Patent No.: US 8,362,259 B2
(45) Date of Patent: Jan. 29, 2013

(54) PROCESS FOR THE PREPARATION OF ESOMEPRAZOLE MAGNESIUM IN A STABLE FORM

(75) Inventor: Renata Toplak Casar, Ljubljana (SI)

(73) Assignee: Lek Pharmaceuticals, D.D., Ljubljana (SI)

( * ) Notice: Subject to any disclaimer, the term of this patent is extended or adjusted under 35 U.S.C. 154(b) by 496 days.

(21) Appl. No.: 12/506,662

(22) Filed: Jul. 21, 2009

(65) Prior Publication Data

US 2010/0016370 A1   Jan. 21, 2010

(30) Foreign Application Priority Data

Jul. 21, 2008  (EP) .................................... 08160826

(51) Int. Cl.
*C07D 401/12*   (2006.01)
(52) U.S. Cl. .................................................. 546/273.7
(58) Field of Classification Search ................. 546/273.7
See application file for complete search history.

(56) References Cited

FOREIGN PATENT DOCUMENTS

| | | |
|---|---|---|
| CA | 2166794 | 1/1995 |
| CA | 2254572 A1 | 10/1999 |
| EP | 0 005 129 A1 | 10/1979 |
| EP | 0 124 495 A2 | 11/1984 |
| EP | 1 230 237 | 8/2002 |
| EP | 1 375 497 A1 | 1/2004 |
| WO | WO 94/27988 A1 | 12/1994 |
| WO | WO 95/01977 A1 | 1/1995 |
| WO | WO 97/41114 A1 | 11/1997 |
| WO | WO 98/54171 A1 | 12/1998 |
| WO | WO 01/36572 A1 | 5/2001 |
| WO | WO 01/87831 A2 | 11/2001 |
| WO | WO 2004/020436 A1 | 3/2004 |
| WO | WO 2004/037253 A1 | 5/2004 |
| WO | WO 2004/046134 A2 | 6/2004 |
| WO | WO 2004/076440 A1 | 9/2004 |
| WO | WO 2004/089935 A1 | 10/2004 |
| WO | WO 2006/003163 A1 | 1/2006 |
| WO | WO 2006/096709 A2 | 9/2006 |
| WO | WO 2007/031845 A2 | 3/2007 |
| WO | WO 2007/071753 A2 | 6/2007 |
| WO | WO 2007/140608 A1 | 12/2007 |
| WO | WO 2008/102145 A2 | 8/2008 |

OTHER PUBLICATIONS

Kirk-Othmer Encyclopedia of Chemical Technology, vol. 8, p. 95-147 (2002).*

* cited by examiner

*Primary Examiner* — Patricia Morris
(74) *Attorney, Agent, or Firm* — Arent Fox LLP (57) ABSTRACT

There is provided a process for preparing purified esomeprazole magnesium, comprising the steps of: providing esomeprazole magnesium; contacting said esomeprazole magnesium with a non-solvent comprising an aqueous component up to a maximum content defined by water saturation in the non-solvent; and recovering purified esomeprazole magnesium formed from the contacting step. The process is particularly suitable to obtain esomeprazole magnesium dihydrate, especially form A. The esomeprazole magnesium obtained is remarkably pure, stable and is resistant to form interchangeability.

14 Claims, 4 Drawing Sheets

PROCESS FOR THE PREPARATION OF ESOMEPRAZOLE MAGNESIUM IN A STABLE FORM

CROSS-REFERENCE TO RELATED APPLICATION

This application claims priority to European Patent Application No. 08160826.7, filed on Jul. 21, 2008, the contents of which are incorporated herein by reference in their entirety.

FIELD OF THE INVENTION

The present invention relates in general to the field of pharmaceutical compositions and in particular to the preparation of a salt of esomeprazole, in particular magnesium salt of esomeprazole, which may be used in a pharmaceutical composition.

BACKGROUND OF THE INVENTION

The compound known under the generic name omeprazole is disclosed in EP 0 005 129.

Omeprazole is useful for inhibiting gastric acid secretion and has gastric mucosa protective activity in mammals and man. Omeprazole may be used for prevention and treatment of gastric acid related disorders and gastrointestinal inflammatory diseases in mammals and man, including for example gastritis, gastric ulcer and duodenal ulcer.

Certain salts of omeprazole are disclosed in EP 0 124 495. Canadian patent 2166794 disclosed a form of magnesium omeprazole dihydrate, which has a higher degree of crystallinity. This form has a methanol content of less than 0.1%.

Canadian patent application No. 2254572 discloses a process for the production of magnesium omeprazole crystalline dihydrate.

The S-enantiomer of omeprazole commonly referred as esomeprazole is said to have improved pharmacokinetical properties which give an improved therapeutic profile such as lower degree of inter-individual variation (WO 94/27988). Esomeprazole magnesium, the generic name for magnesium bis(5-methoxy-2-[(S)-[(4-methoxy-3,5-dimethyl-2-pyridinyl)methyl]sulfinyl]-1H-benzimidazole), is a well-known gastric proton-pump inhibitor and has been commercially available from AstraZeneca under the brand name NEXIUM since 2001.

WO 94/27988 describes a solid form of esomeprazole magnesium, WO 95/01977 describes solid omeprazole magnesium with a degree of crystallinity over 70%.

WO 98/54171 describes a magnesium salt of esomeprazole trihydrate characterized by being highly crystalline and stable. It discloses also polymorphic forms (A and B) of esomeprazole magnesium salt dihydrate and processes for their preparation using esomeprazole potassium salt as an intermediate.

WO 04/046134 describes a crystalline esomeprazole magnesium salt trihydrate form II wherein the term trihydrate is used to define a crystalline material in which water molecules are bound in the crystalline lattice. WO 04/089935 provides new polymorphic forms of crystalline esomeprazole magnesium trihydrate, hemihydrate and monohydrate. WO 07/031845 discloses novel polymorphs of esomeprazole magnesium trihydrate (G1 and G2) and processes for their preparation. In addition, a new process for preparing amorphous esomeprazole magnesium is presented. Therefore the preparation of esomeprazole magnesium trihydrate may suffer on repeatability because many forms are possible which could be interchangeable.

Numerous patent applications WO 01/87831, WO 04/037253, WO 04/020436, WO 06/096709, and WO 07/0710753 describe amorphous esomeprazole magnesium with various amounts of water and residual solvents. Again no clear procedure for a unique form can be concluded.

It is generally known that safety and also stability of an active pharmaceutical ingredient depends among other factors strongly upon residual solvents content.

To diminish the effect of residual solvents they should be all removed to the highest possible extend from an active substance.

EP 1 230 237 describes a procedure of removing residual solvents in omeprazole magnesium and EP 1 375 497 a procedure of removing residual solvents in esomeprazole magnesium by flash evaporation but the products have unrepeatable low crystallinity between amorphous and a degree of crystallinity around 25% and still contain various amounts of residual solvents.

The object of the present invention thus was to provide a process for preparing esomeprazole magnesium in a purified and stable form and in repeatable manner even if scaled up, and to correspondingly provide such a purified, stable and reproducible form of esomeprazole magnesium.

SUMMARY OF THE INVENTION

The present invention provides the following items including main aspects and preferred embodiments, which respectively alone and in combination particularly contribute to solving the above object and eventually provide additional advantages:

(1) A process for preparing purified esomeprazole magnesium, comprising the steps of:
  providing esomeprazole magnesium;
  contacting said esomeprazole magnesium with a non-solvent comprising an aqueous component up to a maximum content defined by water saturation in the non-solvent; and
  recovering purified esomeprazole magnesium formed from the contacting step.

As used herein, the term "non-solvent" is meant as a solvent or mixture of solvents in which the provided esomeprazole magnesium is insoluble or poorly soluble. A suitable non-solvent can be defined by showing a maximum solubility of 5 g/L, preferably maximum solubility of 3 g/L.

The non-solvent is made wet ("wet non-solvent") by adding an aqueous component. As used herein, the term "aqueous component" means water, or a mixture of water with a water-soluble organic solvent. The aqueous component is preferably water alone. Suitable water-soluble organic solvents which can be included into the aqueous component are alcanols, e.g. methanol or ethanol; ketones, e.g. acetone; dipolar aprotic solvents, e.g. DMF or DMSO; respectively alone or in combination, without being limited thereto. Addition of a water-soluble organic solvent to the aqueous component is possible in order to slightly increase solubility of water in some non-solvents such as ethers. But the amount of the added water-soluble organic solvent should be small, preferably very small in order to prevent interchangeability or conversion to some other polymorphic form. Amount of the a water-soluble organic solvent in the mixture therefore preferably does not exceed 5 wt.-%, more preferably does not exceed 2.5 wt.-%.

Amount of the aqueous component, preferably water alone, in the non-solvent is preferably at least 1 wt.-% up to water saturation, preferably up to 5 wt.-%.

It has been surprisingly found that during a contact with a wet non-solvent which is obtained by including a small amount of an aqueous component and in particular water alone in an amount of maximally water saturation, a product is obtainable which has a remarkable chemical and physical stability and thus, also due to very low content of residual solvent, is valuable as an active pharmaceutical ingredient. It is feasible to repeatedly yield stable and pure esomeprazole magnesium in crystal form. Although not bound to any theory, it is believed that during the wet non-solvent treatment, esomeprazole magnesium undergoes a beneficial and stabilising structural rearrangement, while at the same time allowing to reduce solvent components of the starting esomeprazole magnesium. The contacting step is typically carried out for a time sufficient to obtain the desired purification effect and preferably the stabilising effect. A treatment period of 10 min to 48 hours may be suitable, a period of 0.5 to 24 hours, especially of 1 to 8 hours being preferred.

(2) The process according to item (1), wherein said non-solvent is selected from the group consisting of esters and ethers.

(3) The process according to item (1) or (2), wherein said non-solvent is selected from the group consisting of methyl acetate, ethyl acetate, isopropyl acetate, diethyl ether, diisopropyl ether and methyl t-butyl ether.

(4) The process according to any one of items (1) to (3), wherein said non-solvent is ethyl acetate.

(5) The process according to any one of items (1) to (4), wherein said provided esomeprazole magnesium is in a first polymorphic form, which based on said contacting step is converted into a second polymorphic form of esomeprazole magnesium different from said first polymorphic form.

According to this preferred embodiment, said first, starting form of esomeprazole can be consistently and thus repeatedly converted into a second form of esomeprazole magnesium. As desired, the duration of the contacting step may be limited to obtain a controlled mixture of both first and second forms esomeprazole magnesium.

(6) The process according to any of items (1) to (5), wherein said first polymorphic form of esomeprazole magnesium is defined by at least one form selected from amorphous or any crystalline form or intermediate forms, including especially anhydrous, hydrate, solvate and mixed forms thereof, and wherein said prepared, second polymorphic form of esomeprazole magnesium is esomeprazole magnesium dihydrate. As hydrate, hemihydrate, monohydrate, dihydrate, sesquihydrate, trihydrate are particularly mentioned, and as other solvates, alcoholate such as methanolate and ethanolate; ketonate such as acetonate; esterate such as ethyl acetylate; etherate such as diethyletherate; hydrocarbon solvate such as toluene solvate or alkylchloride such as dichloromethane solvate, are particularly mentioned, without being limited to thereto. Remarkably, the process according to the present invention is specifically tailored to the repeatable and consistent production of the dihydrate form of esomeprazole magnesium, especially in its crystalline form and with high chromatographic purity. In spite a variety of optionally selectable first polymorphic forms, surprisingly the dihydrate form of esomeprazole magnesium can be obtained with high stability and polymorphic purity.

(7) It is thus a useful independent aspect of the present invention to provide a process for preparing esomeprazole magnesium dihydrate, comprising the steps of:
providing esomeprazole magnesium;
contacting said esomeprazole magnesium with a non-solvent comprising an aqueous component up to a maximum content defined by water saturation in the non-solvent; and
recovering esomeprazole magnesium dihydrate formed.

Concerning meanings of expressions, features and preferred embodiments, reference is made to the description above.

(8) The process according to item (7), wherein said provided esomeprazole magnesium is in amorphous form or in dihydrate form B which, upon said contacting step, is respectively converted into dihydrate form A of esomeprazole magnesium.

A conversion of amorphous form or dihydrate form B into dihydrate form A is a remarkably repeatable process and makes the provision of extremely pure and stable form of esomeprazole magnesium feasible. The extend of conversion is made as far as desired; preferably it is a major conversion of at least 50%, more preferably at least 60%.

(9) The process according to any one of items (1) to (8), wherein more than 20% of said purified esomeprazole magnesium formed from the contacting step is crystalline.

(10) The process according to any one of the preceding items, wherein said aqueous component consists of water.

Using water alone as a component of the wet non-solvent makes the treatment particularly effective.

(11) The process according to any one of the preceding items, wherein said provided esomeprazole magnesium was prepared from neutral esomeprazole by reaction with magnesium source.

By this measure a reliable, robust and efficient conversion of neutral form into magnesium salt form of esomeprazole is ensured. This preferred embodiment obviates the need of alkaline salt of esomeprazole such as potassium or sodium salt as intermediary substance. It further ensures high yield and chemical, optical, alkali metal and polymorphic purity of the product.

(12) The process according to any one of items (1) to (11), wherein said provided esomeprazole magnesium is a magnesium salt in amorphous or hydrate or solvate form, optionally containing higher content of residual solvents up to 5% by weight.

(13) The process according to item (12), wherein said esomeprazole magnesium salt is in amorphous, monohydrate form, dihydrate form B or acetone solvate form.

(14) The process according to any one of items (1) to (13), wherein said provided esomeprazole magnesium is provided in solid form.

(15) Crystal form of esomeprazole magnesium with a chromatographic (HPLC) purity of at least 99.0%, obtained by wet non-solvent treatment of esomeprazole magnesium. Any starting form of esomeprazole magnesium can be subjected to the treatment, for example those mentioned as the first polymorphic form in item (6) above. Treatment can be done by contacting such starting form of esomeprazole magnesium with a non-solvent comprising aqueous component, in particular water, up to a maximum content defined by water saturation. Concerning the term "non-solvent", reference is made to the definition under item (1) above.

The process of the present invention not only surely and repeatedly results in high chromatographic purity, but inherently achieves also stable maintenance of magnesium form of esomeprazole without impurity formation even under long-term or stress storage conditions.

(16) Crystal form of esomeprazole magnesium according to item (15), wherein the esomeprazole magnesium subjected to wet non-solvent treatment is provided in solid form.

(17) Crystal form of esomeprazole magnesium according to item (15) or (16), wherein the esomeprazole magnesium subjected to wet non-solvent treatment is provided in amorphous, monohydrate form, dihydrate form B, or acetone solvate form.

(18) Crystal form of esomeprazole magnesium according to any one of items (15) to (17), wherein the non-solvent used for wet non-solvent treatment is a solvent or a mixture of solvents, in which the maximum solubility of esomeprazole magnesium is 5 g/l.

(19) Crystal form of esomeprazole magnesium according to any one of items (15) to (18), wherein the non-solvent used for wet non-solvent treatment is a solvent or a mixture of solvents, in which the maximum solubility of esomeprazole magnesium is 3 g/l.

(20) Crystal form of esomeprazole magnesium according to any one of items (15) to (19), wherein the non-solvent used for wet non-solvent treatment was selected from the group consisting of esters and ethers.

(21) Crystal form of esomeprazole magnesium according to any one of items (15) to (20), wherein the non-solvent used for wet non-solvent treatment was selected from the group consisting of methyl acetate, ethyl acetate, isopropyl acetate, diethyl ether, diisopropyl ether and methyl t-butyl ether.

(22) Crystal form of esomeprazole magnesium according to any one of items (15) to (21), wherein the non-solvent used for wet non-solvent treatment was ethyl acetate.

(23) Crystal form of esomeprazole magnesium with a chromatographic (HPLC) purity of at least 99.7%, preferably at least 99.8%, more preferably at least 99.9% and even at least 99.95% is achievable. Such high purity levels become possible when starting the wet non-solvent treatment with esomeprazole magnesium showing already a chromatographic (HPLC) purity of at least 99.5%.

(24) Crystal form of esomeprazole magnesium according to any one of items (15) to (23), wherein the crystal form of esomeprazole magnesium is obtained as the dihydrate form, in particular Form A. Subjecting esomeprazole magnesium to treatment by wet non-solvent for a time sufficient is particularly suited for repeatedly yielding the dihydrate form stably and at extreme high purity.

(25) Crystal form of esomeprazole magnesium dihydrate with residual content of total organic solvent of 1 wt.-% or below.

Total content of residual organic solvent in crystal form of esomeprazole magnesium dihydrate can be drastically reduced according to the present invention to a range of below about 1 wt.-%, preferably below about 0.5 wt.-%, more preferably below about 0.1 wt.-%, and even below about 500 ppm. When the esomeprazole magnesium salt is—as usual— prepared by procedures conducted in organic solvents, the substantial organic solvent reduction to levels acceptable for pharmaceutical applications, preferably to lie within a range of above 0.00 to 0.10 wt.-%, is a particularly beneficial feature. Conventional solvent removal methods, notably simple drying or evaporation process, are unsuitable to achieve such very low levels. Furthermore, these methods are subject to risks of polymorph conversion or esomeprazole decomposition; especially trying to achieve further reduction by involving harsh conditions for solvent removal tends to decompose esomeprazole magnesium dihydrate crystal form. A suitable method of determining residual content of solvent is by chromatography, typically gas chromatography (GC). Residual water content can be tolerated.

(26) Crystal form of esomeprazole magnesium according to any one of items (15) to (25), wherein the sum of omeprazole related substances other than esomeprazole, including all impurities detectable by HPLC while disregarding solvent impurities, is within a range of 0.05% or below, and is preferably maintained within said range under stress stability testing conditions measured by 60° C./7 days/closed packaging-treatment or 40° C./75% RH/14 days/open vial-treatment.

When the pure and stable form of esomeprazole magnesium, preferably dihydrate form and especially Form A described above, is prepared according to the present invention, unique chemical and physical stability features are obtained as indicated, combined for example with a chromatographic (HPLC) purity of esomeprazole magnesium dihydrate significantly higher than 99.7%, e.g. at least 99.8%. On the other hand, other esomeprazole forms which did not undergo wet non-solvent treatment according to the present invention do not repeatedly meet the purity characteristics, and moreover produce omeprazole related substance impurities at a sum of more than 0.05% under the afore-defined stress stability testing conditions. %-indications correspond to % under the curve of HPLC run.

Figure 1:
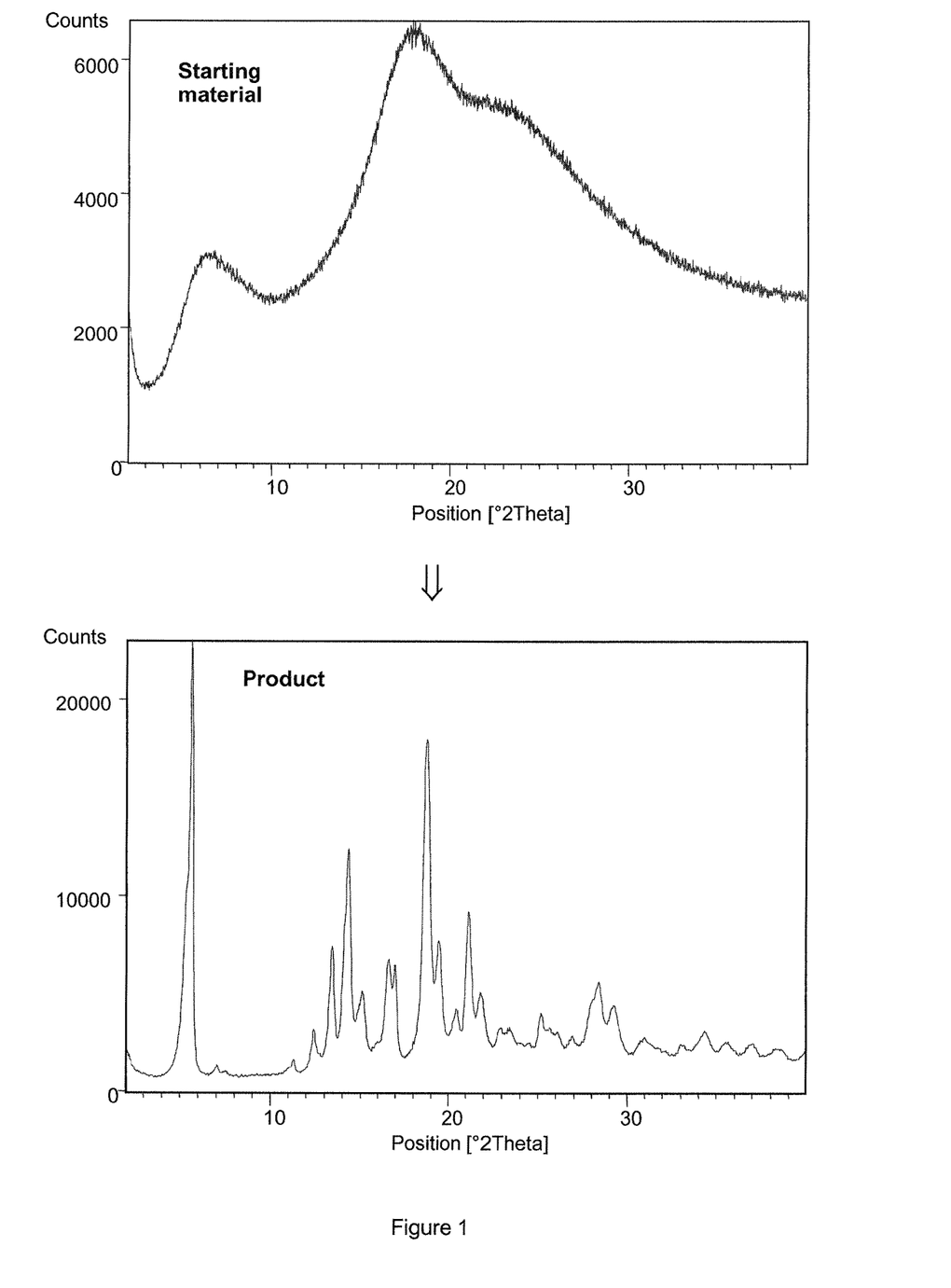
FIG. 1 shows conversion of amorphous esomeprazole magnesium to esomeprazole dihydrate form A according to Example 1 detected by XRPD
Figure 2:
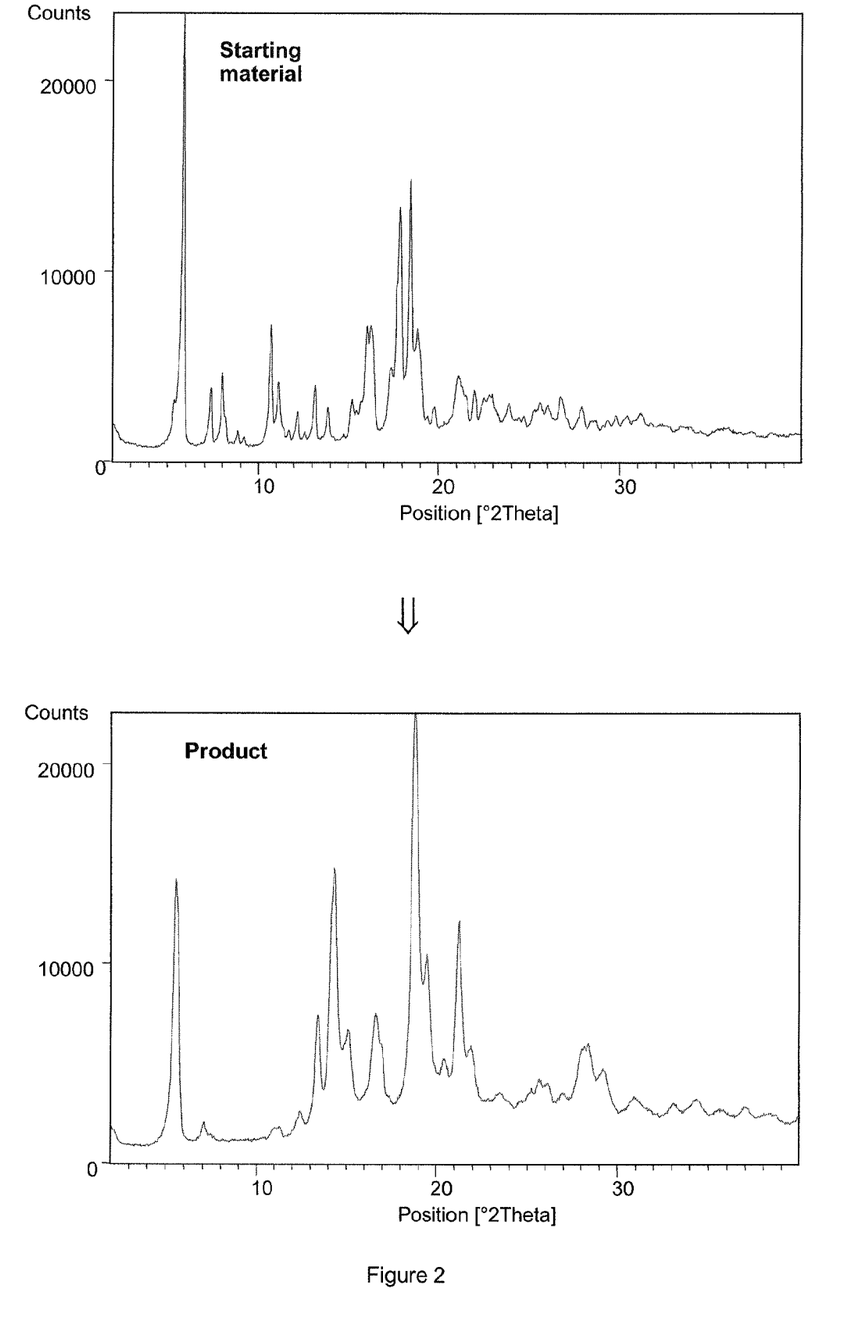
FIG. 2 shows conversion of esomeprazole magnesium dihydrate form B to dihydrate form A according to Example 4 detected by XRPD

(27) Crystal form of esomeprazole magnesium according to one of items (15) to (26) in dihydrate form, preferably in "Form A" being characterized by at least five significant peaks at 2θ values of 5.7, 13.4, 14.4, 18.8 and 21.2 in XRD diffractogram, respectively exactly or ±0.2 degrees 2θ at the indicated 2θ values, preferably being characterized by peaks at 2θ values of 5.7, 13.4, 14.4, 15.1, 16.6, 17.0, 18.8, 19.5, 20.5, 21.2, 21.9, 28.0, 28.4, 29.3 in XRD diffractogram, respectively exactly or ±0.2 degrees 2θ at the indicated 2θ values, preferably as shown in FIGS. 1 and 2.

(28) The crystal form of esomeprazole magnesium dihydrate according to any one of items (15) to (27), with a polymorphic purity being defined by being essentially free of each of other crystalline forms including anhydrous, hydrate and other solvate polymorphic forms, in particular being essentially free of anhydrous, monohydrate, hemihydrate, sesquihydrate, trihydrate, alcoholate (methanolate, ethanolate) and other solvate (generally defined by organic solvent molecule used during isolation of the dihydrate form, in particular hydrocarbon such as toluene, alkylchlorides, ether and ester solvates) polymorphic forms. As used herein, the term "essentially free" is typically referred to a content of less than 5 wt.-%, preferably less than 2 wt.-% and more preferably less than 1 wt.-%. Residual amorphous form may be tolerated at a higher content such as up to 50 wt.-%, possibly up to 40 wt.-%, corresponding to a degree of crystallinity, calculated according to the method described in WO97/41114, of at least around 50%, preferably at least around 60%.

Since the wet non-solvent treatment of esomeprazole magnesium can be tailored specifically towards the dihydrate form, conversion from the starting form from which treatment was started can be made effective in a manner to substantially reduce the starting form, used either alone or in admixture.

(29) A pharmaceutical preparation comprising the crystal form of esomeprazole magnesium according to any one of items (15) to (28) and a pharmaceutically acceptable excipient.

Owing to the stable and highly pure esomeprazole magnesium, in particular the dihydrate form and especially Form A, repeatedly obtained according to the present invention, it is particularly suited for medical use in a pharmaceutical composition containing usual excipients.

(30) The form of esomeprazole magnesium dihydrate according to any one of items (15) to (28), and the pharmaceutical preparation according to item (29) for use in treatment of a gastrointestinal inflammatory disease or condition. The esomeprazole magnesium forms and the pharmaceutical preparation according to the present invention is particularly suitable as anti-ulcer agent.

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

According to the present invention, a simple industrially applicable process is provided for preparation of chemically and physically stable crystalline esomeprazole magnesium salt with low content of residual solvents (less than 1% by weight, less than 0.5% by weight, less than 0.2% by weight). The most stable crystalline esomeprazole magnesium with low content of residual solvents according to the invention is dihydrate form A according to nomenclature of WO 98/54171. Surprisingly little is known how to prepare dihydrates of esomeprazole magnesium, mentioned in WO 98/54171, in form free of residual solvents by a process which can be scaled to the industrial level. Stable dihydrates of appropriate quality which could be prepared in a repeatable manner provides useful final form of esomeprazole magnesium for pharmaceutical application.

According to literature data (EP 1230237, EP 1375497) residual organic solvents are hardly removed from omeprazole or esomeprazole magnesium salts which are prepared by procedures conducted in organic solvents. Especially, when the prepared product is in amorphous form or in a form with low degree of crystallinity residual solvents are entrapped in solid particles and cannot be easily removed by evaporation or drying. Furthermore, due to molecule(s) of solvent incorporated in a crystal lattice a higher content of residual solvents that can not be reduced by simple drying or evaporation, is characteristic also for products in solvated form. By the term "simple drying or evaporation process" we understand processes conducted by conventional methods at conditions (temperature, reduced pressure) that do not effect quality of the obtained product regarding purity or physical properties.

Esomeprazole can be prepared by enantioselective chemical reaction—notably by oxidation of sulphide-, by separation of S-enantiomer from racemate (enantiopurification), via diastereoisomeric derivatisation of omeprazole or by any other suitable process. Preferred is separation by chiral chromatography of racemic omeprazole, for example as described in WO 07/071753.

When the process is started with neutral esomeprazole, it can be transferred into magnesium salt directly by reaction with magnesium source, or via other salt forms followed by conversion into magnesium salt by adding magnesium salt. The magnesium source may be selected from the group consisting of magnesium sulphate, magnesium chloride, magnesium 2-ethyl-hexanoate, magnesium citrate, magnesium stearate, magnesium ascorbate, magnesium acetate, magnesium ethanolate, magnesium methanolate, and mixtures thereof. Magnesium methanolate is preferred. Preferably, the starting substance is obtained by reacting esomeprazole with magnesium methanolate as a magnesium source in methanol solution and further precipitating the substance by addition of non-solvent (e.g. ether, acetate) or addition of crystallizing media (e.g. mixture of acetone and water).

It is prepared from crude esomeprazole magnesium salt in amorphous or hydrate or solvate, which can be obtained by any known process for preparation of amorphous or hydrate or solvate form of esomeprazole magnesium.

The process according to the present invention does not require any alkaline salt of esomeprazole as intermediary substance and it ensures high yield and purity (chemical, optical, alkali metal, polymorphic) of the product. For example, preparation of esomeprazole magnesium dihydrate form A and form B previously described in WO 98/54171 involves a two-step procedure using esomeprazole potassium salt as an intermediate which is further converted with $MgSO_4 \times 7H_2O$ to magnesium salt of esomeprazole and crystallized from a mixture of methanol, acetone and water. The procedures for preparation of both polymorphic forms of esomeprazole magnesium dihydrate according to WO 98/54171 are very similar and do not ensure reproducible formation of a product of polymorphic purity.

Surprisingly, it was discovered that esomeprazole magnesium salt in amorphous or hydrate or solvate (monohydrate, hemihydrate, dihydrate form B, acetone solvate) form, optionally containing higher content of residual solvents (up to 5% by weight), can be transformed into chemically and physically stable and pure esomeprazole magnesium form, in particular to dihydrate form, and especially to form A having low content of residual solvents by a simple process. The process can preferably yield improved product of dihydrate form A. Transformation occurs by simple digestion process of the starting material in a non-solvent containing small amount of water (wet non-solvent). As digestion we denote a process of suspending a substance in a solvent or a mixture of solvents in which it is insoluble or poorly soluble (commonly briefly denoted as "non-solvent") and stirring the suspension for a certain period of time, preferably 0.5-24 hours, most preferably 1-8 hours. A non-solvent is preferably selected from a group of esters, preferably acetates (methyl acetate, ethyl acetate, isopropyl acetate) or from a group of ethers (diethyl ether, diisopropyl ether, methyl t-butyl ether), most preferably ethyl acetate is used. The non-solvent contains a small amount of water, preferably from 1% to saturation. Most preferably ethyl acetate with up to 5% by weight of water is applied in the process. During the process of digesting the starting material esomeprazole magnesium salt in amorphous or hydrate or solvate form is converted into more physically stable crystal structure of esomeprazole magnesium, especially by targeting to esomeprazole magnesium dihydrate and in particular its form A. After recovery and drying of the obtained precipitate, a product with low content of residual solvents is produced by simple drying or evaporation process. No drying in an atmosphere with increased relative humidity or any special treatment is needed to try to eliminate residual solvents. Thus, wet solvent treatment allows the isolated compound (especially dihydrate form A) to treat further to thereby easily and gently remove residual solvents further by simple drying or evaporation process without any risk of changes of polymorphic or chemical characteristics.

On the other hand polymorphic forms conventionally prepared in organic solvents and thus not being in a proper condition as according to the present invention, which are then defined by other forms, content of the residual organic solvents can be lowered only by drying the product under harsh conditions or by applying special techniques and this is likely to cause changes in polymorphic or chemical purity.

According to the particularly preferred embodiment, conversion of esomeprazole magnesium of less defined forms, low crystalline forms, mixture of forms, amorphous or of less thermodynamically stable forms such as esomeprazole magnesium dihydrate form B into esomeprazole magnesium dihydrate form A by the disclosed procedure (Scheme 1) is a highly repeatable process. The conversion was monitored by XRPD and DSC analysis. Comparison of XRPD diffractograms and DCS thermograms of starting materials and products is presented in FIGS. 1-4.

Scheme 1

Further, besides thermodynamic stability esomeprazole magnesium dihydrate form A, prepared according to the preferred embodiment of the invention, exhibits greater chemical stability in comparison of some other forms. Illustratively, it was tested under regular pharmaceutical tests such as stress condition test (Table 1) and was compared with chemical stability of the starting amorphous esomeprazole magnesium or esomeprazole Mg dihydrate form B (Table 2).

TABLE 1

The results of 14 days stress stability testing of esomeprazole Mg dihydrate form A

| | Esomeprazole magnesium dihydrate form A | | |
|---|---|---|---|
| Storage conditions | Initial analysis | 60° C. | 40° C./75 RH, open dish |
| Time of testing | | 7 days | 14 days |
| Packaging | | vial | open vial |
| HPLC - Related substances and degradation products: | | | |
| Sum | | ≦0.05 | ≦0.05 |
| Chromatographic purity | 99.85 | 99.82 | 99.85 |

TABLE 2

The results of 14 days stress stability testing of reference esomeprazole
Mg samples (amorphous and dihydrate form B). Defined impurities represent
pharmacopoeial ones (EuPharma)

| | Amorphous esomeprazole magnesium | | | Esomeprazole magnesium dihydrate form B | | |
|---|---|---|---|---|---|---|
| Storage conditions | Initial analysis | 60° C. | 40° C./75 RH, open dish | Initial analysis | 60° C. | 40° C./75 RH, open dish |
| Time of testing | | 7 days | 14 days | | 7 days | 14 days |
| Packaging | | vial | open vial | | vial | open vial |
| HPLC - Related substances and degradation products (RRt): | | | | | | |
| 0.10 | | | 0.04 | | | |
| 0.11 | | 0.12 | 0.09 | | | |
| 0.16 | 0.06 | 0.18 | 0.07 | | | |
| 0.20 | | 0.06 | 0.04 | | | |
| OMP-benzimidazole (Ph. Eur. Imp. A) | | 0.06 | 0.04 | | | |
| OMP-N-oxide (Ph. Eur. Imp. E) | | 0.03 | | | | |
| OMP-N-sufone (Ph. Eur. Imp. D) | | 0.03 | | | | |
| 1.45 | 0.04 | 0.15 | 0.06 | | | |
| 1.59 | | | | | | 0.06 |
| 1.61 | | | | | | 0.06 |
| 2.20 | | 0.07 | 0.09 | | | |
| 2.25 | | 0.09 | | | | |
| Omeprazole-N-methyl | | | | | 0.07 | |
| SUM | 0.10 | 0.79 | 0.43 | <0.05 | 0.07 | 0.14 |

Comparing the results of stress stability testing of all three forms of esomeprazole magnesium it can be concluded that esomeprazole magnesium in a form of dihydrate form A obtained according to the present invention represents chemically the most stable form.

In addition, also physical stability of esomeprazole magnesium dihydrate form A obtained according to the present invention was tested. The results of the testing prove that the polymorphic form A is stable under the described stress conditions (14 days 40° C./75% relative humidity, 7 days 60° C.).

The products were analyzed by following methods:

X-Ray powder diffraction method:

Conditions for obtaining powder X-ray diffraction (XRPD) patterns: The powder X-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40°2θ in steps of 0.033°2θ and the measurement time of 50 seconds per step. Variable divergence and antiscatter slits were used to maintain 12 mm of sample length irradiated.

Differential Scanning Calorimetry:

Conditions for obtaining DSC thermograms: Thermograms were obtained with Mettler Toledo DSC822e differential scanning calorimeter. The sample (4-6 mg) was placed in an unsealed aluminium pan with a hole and heated at 5° C./min in the temperature range from 30° C. to 200° C.

IR Spectroscopy Method:

Conditions for obtaining infrared spectra: Fourier transform infrared (FTIR) spectra were recorded with a Nicolet Nexus spectrometer. Spectra over a range of 4000 to 400 cm-1 with a resolution of 2 cm$^{-1}$ (16 scans) were recorded on KBr tablets.

The present invention is illustrated but in no way limited by the Examples 1-4. Examples 1, 2 show preparation of esomeprazole magnesium dihydrate form A from amorphous esomeprazole magnesium. Example 3, 4 represents preparation of esomeprazole magnesium dihydrate form A from esomeprazole magnesium dihydrate form B.

EXAMPLES

Preparation of Starting Materials

Amorphous esomeprazole magnesium was prepared according to the examples described in the patent application WO 07/071753 or by any other process described in the patent or scientific literature.

Esomeprazole magnesium dihydrate form B was prepared by any process described in patents (e.g. WO 98/54171) or scientific literature, preferably according to the following procedure:

A stoichiometric amount of 7.6 wt.-% methanolic solution of magnesium methanolate (18.1 mL) was added to the solution of 9.0 g of esomeprazole (99.28% e.e.) in 100 mL of methanol. The obtained reaction mixture was stirred at room temperature for 1 hour allowing to form esomeprazole magnesium salt in the meantime. After addition of 0.4 mL of water the reaction mixture was further stirred for 30 min. The formed inorganic solid salts were separated from the liquid by filtration through a layer of diatomite filter medium (Celite®). The volume of filtrate was then reduced by evaporation of methanol forming an esomeprazole magnesium solution with concentration 40-45 wt.-%. A mixture of 51 mL of acetone and 2.9 mL of water was added to the concentrate. The mixture was seeded with a 0.05 g of esomeprazole magnesium dihydrate form B. After a few minutes a precipitate was formed and the suspension was stirred for 4 hours. The product was filtered off, washed twice with 10 mL of a mixture of acetone and methanol (4/1(V/V)). The wet filter cake was dried for 20 hours at reduced pressure (200 mbar). 8.00 g of esomeprazole magnesium dihydrate form B was obtained (99.84% e.e. determined by chiral HPLC, 100% purity determined by HPLC, 6.1% of water content determined by Karl- Fisher, 1.98% of residual solvents content (methanol, acetone) as determined by GC).

Example 1

Figure 3:
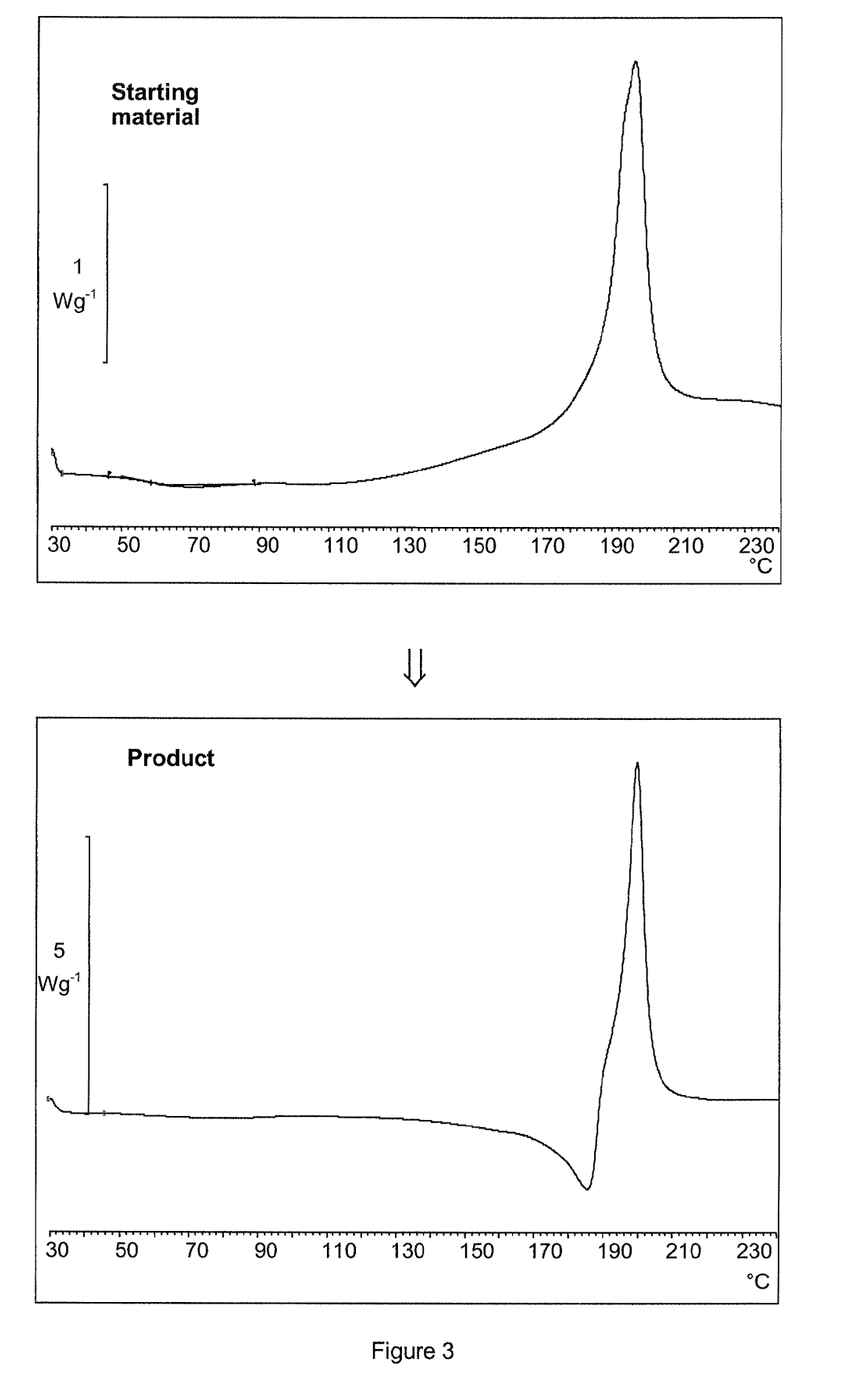
FIG. 3 shows conversion of amorphous esomeprazole magnesium to esomeprazole dihydrate form A according to Example 1 detected by DSC

200 mL of ethyl acetate saturated with water was added to 18 g of amorphous esomeprazole magnesium (99.88% purity determined by HPLC, 4.8% of water content determined by Karl-Fisher, 3.5% of Mg determined by complexometric titration, assay of $C_{34}H_{36}N_6O_6S_2Mg$ 99.42% determined by HPLC, content of residual solvents as determined by GC: 0.25% of methanol, 1.14% of methyl t-butyl ether, XRPD diffractogram of the starting material is presented in the FIG. 1, DSC thermogram in the FIG. 3). The suspension was stirred for 2 hours at room temperature. Then the digested product was filtered off and washed with 10 mL of ethyl acetate. The wet filter cake was dried for 48 hours at 40° C. in vacuum. 16.31 g of esomeprazole magnesium dihydrate form A was obtained (99.85% purity determined by HPLC, 5.38% of water content determined by Karl-Fisher, 3.7% of Mg determined by complexometric titration, content of residual solvents as determined by GC: 220 ppm EtOAc, XRPD diffractogram of the product is presented in the FIG. 1, DSC thermogram in the FIG. 3).

Example 2

4.5 L of ethyl acetate saturated with water at 20° C. was added to 200 g of amorphous esomeprazole magnesium (99.54% purity determined by HPLC, 6.82% of water content determined by Karl-Fisher, 0.22% of residual methanol content as determined by GC). The suspension was stirred for 2 hours at 20° C. Then the digested product was filtered off and washed with 500 mL of ethyl acetate. The wet filter cake was dried for 48 hours at 40° C. in vacuum. 186.83 g of esomeprazole magnesium dihydrate form A was obtained (99.79% purity determined by HPLC, 6.41% of water content determined by Karl-Fisher, 3.6% of Mg determined by complexometric titration, 0.07% of residual solvent content as determined by GC).

Example 3

50 mL of ethyl acetate saturated with water was added to 5 g of crystalline esomeprazole magnesium dihydrate form B with higher content of residual solvents (6.1% of water content determined by Karl-Fisher, 1.98% of residual solvents content (methanol, acetone) as determined by GC). The suspension was stirred for 2 hours at room temperature. Then the digested product was filtered off and washed twice with 10 mL of ethyl acetate. The wet filter cake was dried for 72 hours at 35° C. in vacuum giving 4.6 g of esomeprazole magnesium dihydrate form A (residual solvents content: 761 ppm of ethyl acetate as determined by GC).

Example 4

Figure 4:
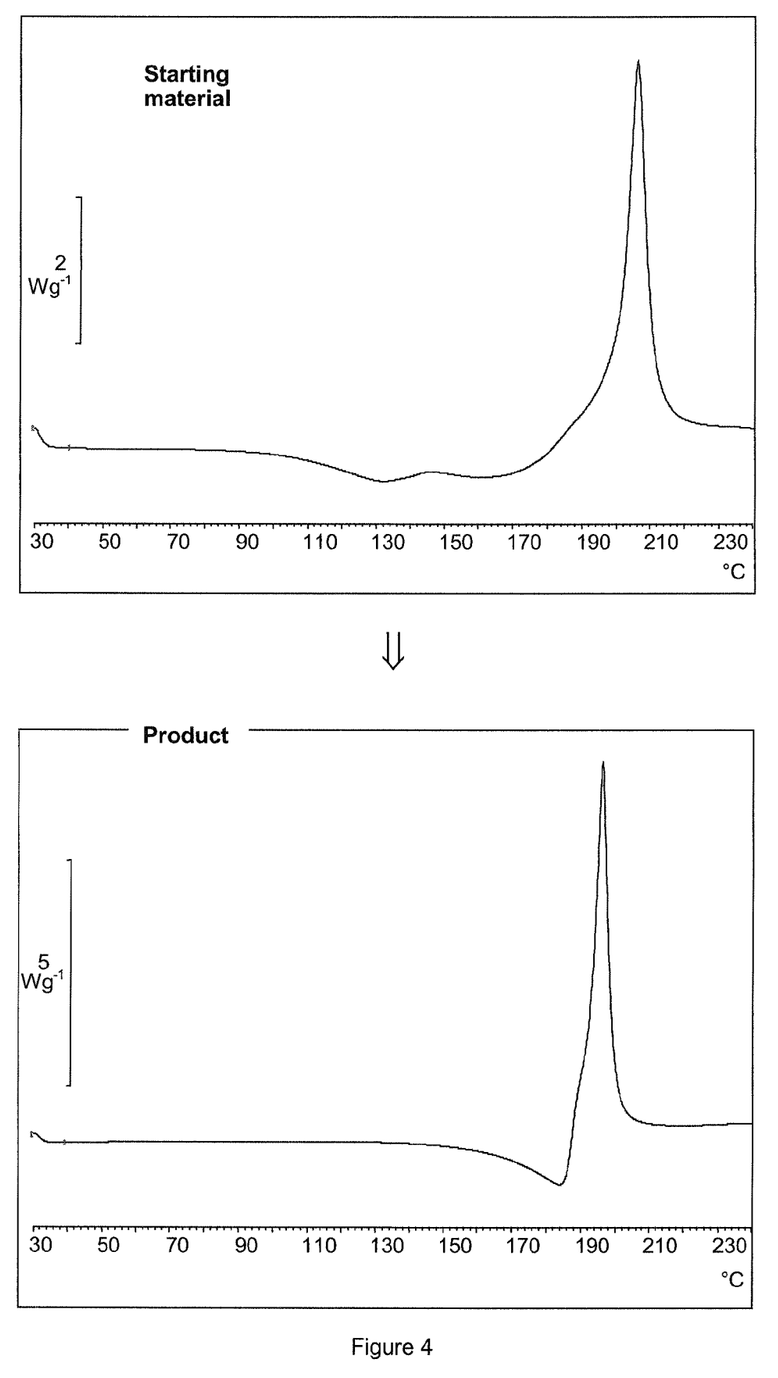
FIG. 4 shows conversion of esomeprazole magnesium dihydrate form B to dihydrate form A according to Example 4 detected by DSC.

200 mL of ethyl acetate saturated with water was added to 20 g of esomeprazole magnesium dihydrate form B (3.4% of Mg determined by complexometric titration, 5.1% of water content determined by Karl-Fisher, XRPD diffractogram FIG. 2, DSC thermogram FIG. 4). The suspension was stirred for 2 hours at room temperature. Then the digested product was filtered off and washed twice with 20 mL of ethyl acetate. The wet filter cake was dried for 48 hours at 35° C. in vacuum. 18.11 g of esomeprazole magnesium dihydrate form A was obtained (XRPD diffractogram of the product is presented in the FIG. 2, DSC thermogram in FIG. 4).

Comparative Example 1

Esomeprazole and Mg methanolate were reacted in methanol according to the prior art process described in the Example 6 of EP 124495. The prepared esomeprazole magnesium was further subjected to evaporation and drying to give a product with residual methanol content of approximately 7%.

Comparative Example 2

Further removing of residual solvents was studied on amorphous esomeprazole magnesium by drying. Substantial removal of residual solvents were achieved only at high temperatures and were accompanied by chemical decomposition.

The invention claimed is:

1. A process for preparing purified esomeprazole magnesium dihydrate form A, comprising the steps of:
    providing esomeprazole magnesium;
    contacting said esomeprazole magnesium with a solvent or mixture of solvents in which the esomeprazole magnesium has a maximum solubility of 5 g/L, wherein said solvent or mixture of solvents comprises an aqueous component provided in an amount up to a maximum content defined by water saturation in the solvent or mixture of solvents; and
    recovering purified esomeprazole magnesium dihydrate form A formed from the contacting step,
    wherein the esomeprazole magnesium dihydrate form A is characterized by having an X-ray diffraction pattern with characteristic peaks (2θ) that are exactly or within ±0.2 degrees 2θ of the following values: 5.7, 13.4, 14.4, 18.8 and 21.2.

2. The process according to claim 1, wherein said provided esomeprazole magnesium is in a first polymorphic form, which based on said contacting step is converted into a second polymorphic form comprising esomeprazole magnesium dihydrate form A, wherein said first polymorphic form is not esomeprazole magnesium dihydrate form A.

3. The process according to claim 2, wherein said first polymorphic form of esomeprazole magnesium is defined by at least one form selected from amorphous, hydrate, and mixed forms thereof, and wherein said prepared, second polymorphic form of esomeprazole magnesium is esomeprazole magnesium dihydrate form A.

4. The process according to claim 1, wherein said aqueous component consists of water.

5. The process according to claim 1, wherein said provided esomeprazole magnesium is a magnesium salt in amorphous or hydrate form, optionally containing higher content of residual solvents up to 5% by weight.

6. The process according to claim 5, wherein said provided esomeprazole magnesium salt is in amorphous form, monohydrate form, or dihydrate form.

7. The process according to claim 1, wherein said provided esomeprazole magnesium was prepared from neutral esomeprazole by reaction with magnesium source.

8. The process according to claim 1, wherein said provided esomeprazole magnesium is provided in solid form.

9. The process according to claim 1, wherein the maximum solubility of esomeprazole magnesium is 3 g/l.

10. The process according to claim 1, wherein said non-solvent is selected from the group consisting of esters and ethers.

11. The process according to claim 1, wherein said non-solvent is selected from the group consisting of methyl acetate, ethyl acetate, isopropyl acetate, diethyl ether, diisopropyl ether and methyl t-butyl ether.

12. The process according to claim 1, wherein said non-solvent is ethyl acetate.

13. The process according to claim 1, wherein more than 20% of said purified esomeprazole magnesium formed from the contacting step is crystalline.

14. The process according to claim 1, wherein the esomeprazole magnesium dihydrate form A is characterized by having an X-ray diffraction pattern with additional characteristic peaks (2θ) that are exactly or within ±0.2 degrees 2θ of the following values: 15.1, 16.6, 17.0, 19.5, 20.5, 21.9, 28.0, 28.4, and 29.3.

* * * * *